United States Patent
Arduini et al.

(10) Patent No.: US 12,201,761 B2
(45) Date of Patent: *Jan. 21, 2025

(54) PERITONEAL DIALYSIS SOLUTION

(71) Applicant: COREQUEST Sagl, Lugano (CH)

(72) Inventors: Arduino Arduini, Arogno (CH); Mario Bonomini, Chieti (IT); Valentina Masola, Pernumia (IT); Giovanni Gambaro, Scorzè (IT)

(73) Assignee: COREQUEST Sagl, Lugano (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/378,985

(22) Filed: Oct. 11, 2023

(65) Prior Publication Data

US 2024/0042115 A1    Feb. 8, 2024

Related U.S. Application Data

(63) Continuation of application No. 18/078,764, filed on Dec. 9, 2022, now Pat. No. 11,964,087, which is a continuation of application No. 17/318,001, filed on May 12, 2021, now Pat. No. 11,779,692.

(60) Provisional application No. 63/026,936, filed on May 19, 2020.

(30) Foreign Application Priority Data

May 19, 2020   (EP) ..................... 20175357

(51) Int. Cl.
| | |
|---|---|
| *A61M 1/28* | (2006.01) |
| *A61K 31/047* | (2006.01) |
| *A61K 31/205* | (2006.01) |
| *A61K 31/7004* | (2006.01) |
| *A61K 47/02* | (2006.01) |
| *A61K 47/10* | (2017.01) |
| *A61K 47/40* | (2006.01) |
| *A61P 7/08* | (2006.01) |

(52) U.S. Cl.
CPC .......... *A61M 1/287* (2013.01); *A61K 31/047* (2013.01); *A61K 31/205* (2013.01); *A61K 31/7004* (2013.01); *A61K 47/02* (2013.01); *A61K 47/10* (2013.01); *A61K 47/40* (2013.01); *A61P 7/08* (2018.01)

(58) Field of Classification Search
None
See application file for complete search history.

(56) References Cited

U.S. PATENT DOCUMENTS

| | | |
|---|---|---|
| 4,574,085 A | 3/1986 | Dolkart et al. |
| 6,822,002 B1 | 11/2004 | Arduini |
| 2008/0138443 A1 | 6/2008 | Arduini |
| 2010/0114012 A1 | 5/2010 | Sandford et al. |
| 2018/0169318 A1 | 6/2018 | Bengtsson |

FOREIGN PATENT DOCUMENTS

| | | |
|---|---|---|
| CN | 108064955 A | 5/2018 |
| WO | 2011107630 A1 | 9/2011 |

OTHER PUBLICATIONS

Bonomini, M., Di Silvestre, S., Di Tomo, P., Di Pietro, N., Mandatori, D., Di Liberato, L., . . . & Arduini, A. (2016). Effect of peritoneal dialysis fluid containing osmo-metabolic agents on human endothelial cells. Drug Design, Development and Therapy, 3925-3932. (Year: 2016).*
ClinicalTrials.gov Identifier: NCT03994471, Efficacy and safety of xylocore peritoneal dialysis. (Elixir), Jun. 21, 2019.
Bonomini et al., "Current opinion on usage of L-carnitine in end-stage renal disease patients on peritoneal dialysis" Molecules, 2019, v 24, n 3449, p. 1-12.
ClinicalTrials.gov Identifier: NCT04001036, Efficacy and safety assessments of a peritoneal dialysis solution containing glucose, xylitol, and L-carnitine in CAPD. Jun. 27, 2019.
Andreoli, M. C. C., & Totoli, C. (2020). Peritoneal dialysis. Revista da Associa<;:ao Medica Brasileira, 66, s37-s44. (Year: 2020).
Chionh, C. Y., Clementi, A., Poh, C. B., Finkelstein, F. 0., & Cruz, D. N. (2020). The use of peritoneal dialysis in heart failure: a systematic review. Peritoneal Dialysis International, 40(6), 527-539. (Year: 2020).

* cited by examiner

*Primary Examiner* — Dale R Miller

(74) *Attorney, Agent, or Firm* — Gregory P. Einhorn; Greer, Burns & Crain, Ltd.

(57) ABSTRACT

In alternative embodiments, provided are solutions for peritoneal dialysis for use for maintaining or restoring the removal of small solutes and fluids in subjects with end-stage renal disease and/or congestive heart failure. In alternative embodiments, such solutions comprise carnitine, xylitol and at least one of glucose, glycerol and polydextrin.

13 Claims, No Drawings

PERITONEAL DIALYSIS SOLUTION

RELATED APPLICATIONS

This U.S. Utility Continuation Patent Application claims the benefit of priority to U.S. patent application Ser. No. 18/078,764 filed Dec. 9, 2022, now pending, which is a continuation of U.S. Ser. No. 17/318,001, filed May 12, 2021, now U.S. Pat. No. 11,779,692 issue date Oct. 10, 2023, which claims benefit of priority under 35 U.S.C. § 119 (e) of U.S. Provisional Application Ser. No. 63/026,936, filed May 19, 2020, now expired; and to EP patent application No. 20175357.1, filed May 19, 2020. The aforementioned applications are expressly incorporated herein by reference in their entirety and for all purposes.

TECHNICAL FIELD

The present invention generally relates to the field of peritoneal dialysis.

In alternative embodiments, provided are solutions for peritoneal dialysis able to maintain or even restore the removal of small solutes and fluid.

BACKGROUND

Peritoneal dialysis (PD) is a viable but under-prescribed method of treating uremic patients and patients with severe congestive heart failure resistant to diuretic therapy (International comparison of peritoneal dialysis prescriptions from the Peritoneal Dialysis Outcomes and Practice Patterns Study (PDOPPS). Wang A Y, Zhao J, Bieber B, Kanjanabuch T, Wilkie M, Marshall M R, Kawanishi H, Perl J, Davies S; PDOPPS Dialysis Prescription and Fluid Management Working Group. Perit Dial Int. 2020 Jan. 17:896860819895356; The use of peritoneal dialysis in heart failure: A systematic review. Chionh C Y, Clementi A, Poh C B, Finkelstein F O, Cruz D N. Perit Dial Int. 2020 Jan. 13:896860819895198).

Treatment-related failure remains a major limitation to the long-term success of peritoneal dialysis therapy.

Concerns about its use centre around the bio-incompatibility of peritoneal dialysis fluids due to their potential for altering the functional and anatomical integrity of the peritoneal membrane. Most of these effects are due to the high glucose content of these solutions, with attendant issues of glucose degradation products (GDPs) generated during heat treatment of glucose-containing solutions and the metabolic effects of the very high glucose concentrations per se.

Glucose is the standard osmotic agent used in PD solutions to induce water flow, and thereby peritoneal ultrafiltration across the peritoneal capillaries in order to remove excess fluid and solutes from the patient's body.

The progressive damage to the peritoneal membrane is evidenced by faster peritoneal solute transport rate and by a decline of ultrafiltration capacity eventually resulting in ultrafiltration failure, which is often characterized by impaired osmotic conductance (Krediet R T, Struijk D G (2013) Peritoneal changes in patients on long-term peritoneal dialysis. Nat Rev Nephrol 9: 419-429).

The observation that these deleterious changes occur upon exposure to conventional glucose-based PD solutions fuels the search for a more biocompatible PD solution. Glucose-based PD solutions developed using multi-chamber bags and characterized by neutral or physiological-pH and low-GDP fluids as compared to conventional predecessors have been labeled as "biocompatible".

However, after over a two decades of investigating the potential benefits of neutral pH low-GDP solutions, limited evidence supporting their true biocompatibility exists (Misra P S, Nessim S J, Perl J. "Biocompatible" Neutral pH Low-GDP Peritoneal Dialysis Solutions: Much Ado About Nothing? Semin Dial. 2017 March; 30(2):164-173; Bartosova M, Schmitt C P (2019) Biocompatible peritoneal dialysis: the target is still way off. Frontiers Physiol 2019; 9:1853).

Given the evidence for the peritoneal membrane toxicity of glucose and its metabolites, many attempts have been made to identify other suitable osmotic agents.

Two such candidate agents are represented by L-carnitine and xylitol.

Peritoneal dialysis solutions containing L-carnitine and glucose (Bonomini M, Pandolfi A, Di Liberato L, Di Silvestre S, Cnops Y, Di Tomo P, D'Arezzo M, Monaco M P, Giardinelli A, Di Pietro N, Devuyst O, Arduini A (2011) L-carnitine is an osmotic agent suitable for peritoneal dialysis. Kidney Int 80: 645-654; Bonomini M, Di Liberato L, Del Rosso G, Stingone A, Marinangeli G, Consoli A, Bertoli S, De Vecchi A, Bosi E, Russo R, Corciulo R, Gesualdo L, Giorgino F, Cerasoli P, Di Castelnuovo A, Monaco M P, Shockley T, Rossi C, Arduini A (2013) Effects of an L-carnitine-containing peritoneal dialysate on insulin sensitivity in patients treated with CAPD: a 4-month, prospective, multicentre randomized trial. Am J Kidney Dis 62(5): 929-938; WO0126649), or solutions containing L-carnitine, low-dose glucose and xylitol (Bonomini M, Di Silvestre S, Di Tomo P, Di Pietro N, Mandatori D, Di Liberato L, Sirolli V, Chiarelli F, Indiveri C, Pandolfi A, Arduini A (2016) Effect of peritoneal dialysis fluid containing osmo-metabolic agents on human endothelial cells. Drug Des Develop Ther 10: 3925-3932; WO 2006 094900) have been evaluated.

In particular, the combination of L-carnitine, low-dose glucose and xylitol has been tested in vitro on endothelial cells (Bonomini, 2016) or on mesothelial cells (WO2006094900) and the effects, respectively, on vascular inflammation and on mesothelial cells growth have been observed.

While considerable evidence in support of the biocompatibility of novel solutions has emerged from cell culture and animal studies, the clinical benefits, especially in terms of removal of small solutes and fluids, as compared to conventional PD solutions are not disclosed nor foreseeable.

Indeed, the use of biocompatible fluids is unsupported by high level clinical evidence.

There was, based on cell culture and animal model findings, widespread optimism and acceptance of what might be termed the biocompatibility hypothesis, the belief that these solutions would preserve the peritoneal membrane, prevent ultrafiltration failure, and perhaps even enhance host defenses and reduce peritonitis rates. The solutions were adopted with particular enthusiasm in Western Europe and East Asia. Results with these solutions have been disappointing. Numerous small randomized trials over the past 15 years have examined their effects on peritoneal transport and, far from improving membrane function, they have been associated in many of these studies with lower ultrafiltration and increased small solute transport in the first 12 months of use compared with conventional solutions (Peter G. Blake; Is the peritoneal dialysis biocompatibility hypothesis dead?; Kidney International, 2018; 94, 246-248; Misra et al., 2017). Therefore the predictivity of in vitro cell systems in testing the biocompatibility of a PD solution doesn't offer any guarantee that this would translate in a favorable clinical effect in human studies in terms of depuration and ultrafiltration performances.

Furthermore, according to the most recent guidelines from the International Society of Peritoneal Dialysis and current clinical practices, dialytic prescription should take into account all the possible parameters describing both removal of solutes and fluids along with quality of life (International comparison of peritoneal dialysis prescriptions from the Peritoneal Dialysis Outcomes and Practice Patterns Study (PDOPPS). Wang A Y, Zhao J, Bieber B, Kanjanabuch T, Wilkie M, Marshall M R, Kawanishi H, Perl J, Davies S; PDOPPS Dialysis Prescription and Fluid Management Working Group. Perit Dial Int. 2020 Jan. 17:896860819895356).

Therefore, there is still the need of peritoneal dialysis solutions able to maintain or restore the removal of solutes and fluids, taking into account also the maintenance of the quality of life, in subjects suffering from end-stage renal disease and/or affected by congestive heart failure.

In particular, there is still the need of solutions for peritoneal dialysis able to maintain or restore the depurative efficacy in such subjects. Also, there is the need of solutions for peritoneal dialysis able to maintain or restore the ultrafiltration in such subjects. Even more in particular, there is the need of solutions overcoming the disadvantages of conventional peritoneal dialysis fluids, especially those containing high doses of glucose, at the same time not impairing or even improving the ability of the subject undergoing peritoneal dialysis to remove small solutes and fluids.

SUMMARY

In alternative embodiments, provided are methods for maintaining or restoring the removal of small solutes and fluids in an individual in need thereof,
  wherein optionally the individual in need thereof is suffering from an end-stage renal disease and/or from congestive heart failure,
  the method comprising: administering intraperitoneally to the individual in need thereof a peritoneal dialysis solution comprising:
  (a) between about 0.02% to 0.05% w/v of carnitine,
  (b) between about 0.50% to 2.50% w/v of xylitol, and
  (c) at least one of: between about 0 to 2.90% w/v of glucose, between about 0 to 8.0% w/v of polydextrin, and between about 0 to 1.30% w/v of glycerol.

In alternative embodiments of methods as provided herein:
  the depurative efficacy and/or ultrafiltration is maintained or restored by administering the peritoneal dialysis solution;
  the restoration of depurative efficacy is an increase of the parameter Kt/V to a value of at least 1.5±0.1, optionally to a value comprised between 1.7±0.1 and 1.8±0.1;
  administering the peritoneal dialysis solution results in an improvement of the removal of small solutes and fluids by the individual in need thereof;
  said improvement of the removal of small solutes and fluids is an improvement of depurative efficacy and/or of ultrafiltration;
  the improvement of the depurative efficacy is an increase of the parameter Kt/v.
  residual kidney function in the individual in need thereof is preserved;
  the peritoneal dialysis solution comprises about 0.02% w/v of carnitine;
  the peritoneal dialysis solution comprises from between about 0.50% to 1.50% w/v of glucose;
  the peritoneal dialysis solution comprises:
  about 0.7% w/v xylitol, about 0.5% w/v glucose and about 0.02% w/v carnitine;
  about 1.5% w/v xylitol, about 0.5% w/v glucose and about 0.02% w/v carnitine;
  about 2.0% w/v xylitol, about 1.5% w/v glucose and about 0.02% w/v carnitine;
  about 0.7% w/v xylitol, about 1.45% w/v glucose and about 0.02% w/v carnitine;
  about 0.7% w/v xylitol, about 2.90% w/v glucose and about 0.02% w/v carnitine; or
  about 1.5% w/v xylitol, about 1.5% w/v glucose and about 0.02% w/v carnitine;
  the peritoneal dialysis solution further comprises one or more ingredients selected from the group consisting of: sodium, calcium, magnesium, chloride, lactate, citrate and bicarbonate;
  the peritoneal dialysis solution comprises: sodium from between about 128 to 134 mmol/l, optionally about 132 mmol/l; calcium from between about 1.2 to 1.8 mmol/l, optionally about 1.3 mmol/l; magnesium from between about 0.25 to 0.75 mmol/l, optionally about 0.5 mmol/l; chloride from between about 90 to 120 mmol/l, optionally about 103.5 mmol/l; lactate from between about 25 to 40 mmol/l, optionally about 35 mmol/l; bicarbonate from between about 0 to 40 mmol/l; or citrate from between about 0 to 10 mmol/l, optionally about 2 or 4 mmol/l; or any combination thereof;
  the peritoneal dialysis solution has a pH comprised between 5.5 and 7.5, optionally a pH of 5.5 or 7.1;
  the peritoneal dialysis solution comprises one of the following groups of compositions:

| | | |
|---|---|---|
| (a) | Xylitol mmol/l | 46 (0.7% w/v) |
| | Glucose mmol/l | 27.7 (0.5% w/v) |
| | L-Carnitine mmol/l | 1.24 (0.02% w/v) |
| | Sodium mmol/l | 132 |
| | Calcium mmol/l | 1.3 |
| | Magnesium mmol/l | 0.5 |
| | Chloride mmol/l | 103.5 and |
| | Lactate mmol/l | 35; |
| (b) | Xylitol mmol/l | 98.6 (1.5% w/v) |
| | Glucose mmol/l | 27.7 (0.5% w/v) |
| | L-Carnitine mmol/l | 1.24 (0.02% w/v) |
| | Sodium mmol/l | 132 |
| | Calcium mmol/l | 1.3 |
| | Magnesium mmol/l | 0.5 |
| | Chloride mmol/l | 103.5 and |
| | Lactate mmol/l | 35; |
| (c) | Xylitol mmol/l | 125 (2.0% w/v) |
| | Glucose mmol/l | 83 (1.5% w/v) |
| | L-Carnitine mmol/l | 1.24 (0.02% w/v) |
| | Sodium mmol/l | 132 |
| | Calcium mmol/l | 1.3 |
| | Magnesium mmol/l | 0.5 |
| | Chloride mmol/l | 103.5, and |
| | Lactate mmol/l | 35; |
| (d) | Xylitol mmol/l | 46 (0.7% w/v) |
| | Glucose mmol/l | 80.3 (1.45% w/v) |
| | L-Carnitine mmol/l | 1.24 (0.02% w/v) |
| | Sodium mmol/l | 132 |
| | Calcium mmol/l | 1.3 |
| | Magnesium mmol/l | 0.5 |
| | Chloride mmol/l | 103.5, and |
| | Lactate mmol/l | 35; |
| (e) | Xylitol mmol/l | 46 (0.7% w/v) |
| | Glucose mmol/l | 162 (2.9% w/v) |
| | L-Carnitine mmol/l | 1.24 (0.02% w/v) |
| | Sodium mmol/l | 132 |

-continued

|     |                  |                  |
| --- | ---------------- | ---------------- |
|     | Calcium mmol/l   | 1.3              |
|     | Magnesium mmol/l | 0.5              |
|     | Chloride mmol/l  | 103.5, and       |
|     | Lactate mmol/l   | 35; or           |
| (f) | Xylitol mmol/l   | 98.6 (1.5% w/v)  |
|     | Glucose mmol/l   | 83 (1.5% w/v)    |
|     | L-Carnitine mmol/l | 1.24 (0.02% w/v) |
|     | Sodium mmol/l    | 132              |
|     | Calcium mmol/l   | 1.3              |
|     | Magnesium mmol/l | 0.5              |
|     | Chloride mmol/l  | 103.5 and        |
|     | Lactate mmol/l   | 35;              | the administering comprises a continuous ambulatory peritoneal dialysis (CAPD) or an automatic peritoneal dialysis (APD);

the administering comprises a nocturnal exchange of peritoneal dialysis solution and/or one or more diurnal exchanges of peritoneal dialysis solution;

the peritoneal dialysis solution is contained, stored and/or delivered in a bag, optionally a single-, dual- or multi-chamber bag;

said peritoneal dialysis solution is in the form of a concentrate or in a dry (e.g., a powder) form;

the administering comprises use of a peritoneal dialysis home machine;

the method prevents kidney and/or peritoneal damage, and the individual in need thereof is a subject in which the ability of the kidney and/or of the peritoneal membrane to remove small solutes and fluids is not yet compromised, and optionally the subject has not yet undergone a peritoneal dialysis treatment;

the individual in need thereof is a subject affected by severe congestive heart failure resistant to diuretic therapy;

when used in peritoneal dialysis in a subject suffering from end-stage renal disease and/or congestive heart failure administration of the peritoneal dialysis solution is able to maintain or restore the removal of small solutes and fluids;

the peritoneal dialysis solution is administered to the individual in need thereof once, twice, three times or four times or more a day;

the volume of the peritoneal dialysis solution administered intraperitoneally for each dose, or dwell, is between about 1 to 3 liters, or between about 2 to 5 liters, optionally between about 1 to 3 liters for CAPD, and between about 2 to 5 liters for APD, and optionally for a pediatric patient the volume of the peritoneal dialysis solution administered is individualized according to intraperitoneal pressure measurements; and/or, the peritoneal dialysis solution is left in the peritoneal cavity of the individual in need thereof for, or the dwell time is, between about 30 minutes up to 12 hours, or between about 1 hour and 10 hours.

It has now been found that a solution comprising:
from 0.02% to 0.05% w/v of carnitine; and
from 0.50% to 2.50% w/v of xylitol; and
from 0 to 2.90% w/v of glucose and from 0 to 1.30% w/v of glycerol and from 0 to 8.0% w/v of polydextrin, wherein at least one of glucose, glycerol and polydextrin is present,
when used in peritoneal dialysis in a subject in need thereof, optionally suffering from end-stage renal disease and/or congestive heart failure, is able to maintain or restore the removal of small solutes and fluids.

In particular, in this embodiment, it is able to maintain or restore the depurative efficacy and/or the ultrafiltration of the subject with respect to conventional glucose solutions.

Therefore, exemplary solutions as provided herein are used for maintaining or restoring the removal of small solutes and fluids, in particular, for maintaining or restoring depurative efficacy and/or ultrafiltration, in a patient suffering from end-stage renal disease and/or from congestive heart failure.

The solution and its uses and particular embodiments thereof will be described in the following.

DETAILED DESCRIPTION

The manufacture of the solutions for peritoneal dialysis described as provided herein is well within the knowledge and abilities of the skilled in the art. An example of useful reference is WO 2004/052269 and related references.

In alternative embodiments, w/v % is intended to be weight/volume percentage concentration.

This is a well-known way in the field to express the concentration of an ingredient in a solution.

In alternative embodiments, carnitine means L-carnitine or a lower alkanoyl derivative thereof, or optionally L-carnitine.

A lower alkanoyl derivative is a $C_2$-$C_8$ acyl derivative, such as, for example acetyl, propionyl, butyryl, isobutyryl, valeryl, isovaleryl, hexanoyl, octanoyl and all their possible isomers. $C_2$-$C_4$ acyl-carnitine are preferred, acetyl-carnitine being particularly preferred.

Normally, carnitine, in particular L-carnitine is used in the form of inner salt. If suitable, a pharmaceutically acceptable salt can be used. Definition and examples of said salts are provided in WO 01/26649.

Examples of pharmaceutically acceptable salts are chloride, bromide, orotate, acid aspartate, acid citrate, magnesium citrate, acid phosphate, fumarate and acid fumarate, magnesium fumarate, lactate, maleate and acid maleate, mucate, acid oxalate, pamoate, acid pamoate, acid sulfate, glucose phosphate, tartrate, acid tartrate, magnesium tartrate, 2-amino ethansulfonate, magnesium 2-amino ethansulfonate, choline tartrate and trichloroacetate.

L-carnitine and its lower alkanoyl derivatives, as well as the pharmaceutically acceptable salts thereof, are widely marketed. Also, their preparation is exhaustively provided in literature, see for example the patent references WO 01/26649 and WO2006094900.

Reference can be made to the cited documents WO 01/26649 and WO2006094900 and the art referred therein for a description of the use of carnitine in peritoneal dialysis.

In the solutions herein described, carnitine is present in a concentration ranging from 0.02% to 0.05% w/v. A preferred range is from 0.02% to 0.03% w/v. Preferred concentrations are 0.02%, 0.025%, 0.03%. In a preferred embodiment of the present invention, carnitine is present in the solution at a concentration of 0.02% w/v.

In the solutions herein described, xylitol is present in a concentration ranging from 0.50% to 2.50% w/v. A preferred range is from 0.7% to 2.0% w/v. Another preferred range is from 0.7% to 1.5% w/v. Preferred concentrations are 0.7, 0.75, 1.0, 1.5, 2.0% w/v.

Reference can be made to the above mentioned Bonomini, 2016, and WO2006094900 and the art referred therein for a description of the use of xylitol in peritoneal dialysis.

In the solutions herein described, at least one of glucose, glycerol and polydextrin is present. Optionally, glucose is present.

In the solutions herein described, glucose is present in a concentration ranging from 0 to 2.90% w/v. A preferred range is from 0.30% to 2.90% w/v; a further preferred range is from 0.5% to 2.0% w/v; an even further preferred range is from 0.5% to 1.5% w/v. Preferred concentrations are 0.3%, 0.5%, 1.45%, 1.5%, 2.5% and 2.9% w/v.

Glucose can also be in hydrate form. In an embodiment, glucose is glucose monohydrate.

Glycerol is present in a concentration ranging from 0 to 1.30% w/v, optionally from 0.11 to 1.3% w/v. Preferred concentrations are 0.11%, 0.15%, 0.44%, 0.58%, 1.15% and 1.3% w/v.

In some embodiments, both glucose and glycerol are present. In this embodiment, glucose is optionally in a concentration of about 0.3% w/v.

In an alternative embodiment, only glucose is present.

Polydextrin is present in a concentration from 0 to 8.0% w/v, optionally from 4 to 7% w/v.

Preferred concentrations are 4% and 7% w/v.

In an embodiment, only polydextrin is present.

In further embodiments, both polydextrin and glucose or both polydextrin and glycerol are present.

All these agents are well known in the field and widely marketed.

In a preferred embodiment, the solution comprises 0.7% w/v xylitol, 0.5% w/v glucose and 0.02% w/v carnitine.

In alternative embodiments, the solution comprises 1.5% w/v xylitol, 0.5% w/v glucose and 0.02% w/v carnitine.

In alternative embodiments, the solution comprises 2.0% w/v xylitol, 1.5% w/v glucose and 0.02% w/v carnitine.

In further embodiments, the solution has one of the following compositions:

0.7% w/v xylitol, 0.5% w/v glucose and 0.02% w/v carnitine;
0.7% w/v xylitol, 1.45% w/v glucose and 0.02% w/v carnitine;
0.7% w/v xylitol, 2.9% w/v glucose and 0.02% w/v carnitine;
1.0% w/v xylitol, 2.5% w/v glucose and 0.02% w/v carnitine;
0.7% w/v xylitol, 0.5% w/v glucose and 0.025% w/v carnitine;
1.5% w/v xylitol, 0.5% w/v glucose and 0.025% w/v carnitine;
2.0% w/v xylitol, 1.5% w/v glucose and 0.025% w/v carnitine;
0.7% w/v xylitol, 0.5% w/v glucose and 0.03% w/v carnitine;
1.5% w/v xylitol, 0.5% w/v glucose and 0.03% w/v carnitine;
2.0% w/v xylitol, 1.5% w/v glucose and 0.03% w/v carnitine;
0.7% w/v xylitol, 0.11% w/v glycerol, 0.3% w/v glucose and 0.02% w/v carnitine;
1.0% w/v xylitol, 0.44% w/v glycerol, 0.3% w/v glucose and 0.02% w/v carnitine;
1.0% w/v xylitol, 1.15% w/v glycerol, 0.3% w/v glucose and 0.02% w/v carnitine;
0.7% w/v xylitol, 0.58% w/v glycerol, 0.3% w/v glucose and 0.02% w/v carnitine;
0.7% w/v xylitol, 1.30% w/v glycerol, 0.3% w/v glucose and 0.02% w/v carnitine;
0.7% w/v xylitol, 0.11% w/v glycerol, 0.3% w/v glucose and 0.025% w/v carnitine;
1.0% w/v xylitol, 0.44% w/v glycerol, 0.3% w/v glucose and 0.025% w/v carnitine;
1.5% w/v xylitol, 4.0 w/v polydextrin and 0.02% w/v carnitine,
1.5% w/v xylitol, 7.0 w/v polydextrin and 0.02% w/v carnitine,
1.5% w/v xylitol, 4.0 w/v polydextrin and 0.025% w/v carnitine,
1.5% w/v xylitol, 7.0 w/v polydextrin and 0.03% w/v carnitine.

In alternative embodiments, a solution comprising 1.5% w/v xylitol, 4.0 w/v polydextrin and 0.02% w/v carnitine is for use in a subject suffering from congestive heart failure.

In alternative embodiments, a solution comprising 1.5% w/v xylitol, 7.0 w/v polydextrin and 0.02% w/v carnitine is for use in a subject suffering from ESRD with ultrafiltration failure.

The solution can further comprise one or more ingredients such as electrolytes and buffers.

In particular, such further ingredient can be selected from the group consisting of: sodium, calcium, magnesium, chloride, lactate, citrate and bicarbonate.

Optionally, the solution further comprises:

Sodium from 128 to 134 mmol/l, optionally 130 or 132 mmol/l;
Calcium from 1.2 to 1.8 mmol/l, optionally 1.3 mmol/l;
Magnesium from 0.25 to 0.75 mmol/l, optionally 0.5 mmol/l;
Chloride from 90 to 120 mmol/l, optionally 103.5 mmol/l;
Lactate from 25 to 40 mmol/l, optionally 35 mmol/l;
Citrate from 0 to 10 mmol/l, optionally 2 or 4 mmol/l;
Bicarbonate from 0 to 40 mmol/l.

The solution can have a pH comprised between 5.5 and 7.5. Optionally it has a pH of about 5.5 or 7.1.

The solution can contain further osmotic agents. Osmotic agent is a solute contained in a concentration sufficient to create an osmotic pressure to replace kidney function by diffusion from the patient's blood across the peritoneal membrane into the solution.

Osmotic agents for peritoneal dialysis are well-known in the art and optionally the agent is selected from the group consisting of: galactose; polyglucose; polyglycerol, fructose; sorbitol; amino acids, glycerol tripyruvate (tripyruvin), a single peptide, a mixture of peptides, polypeptides, pyruvate compound in the form of a sugar-pyruvate ester, a polyol-pyruvate ester, pyruvate thioester, a dihydroxyacetone-pyruvate ester and a dicarboxylic acid, in particular a $C_2$-$C_{15}$-dicarboxylic acid, such as dodecanedioic acid. Other osmotic agents, albeit not specifically mentioned here, are not excluded from the present invention. Osmotic agents for use in peritoneal dialysis are commonly available and a description of these agents can be found in technical literature, for example the above mentioned WO01/26649, US5.126.373.

Conveniently, the solution according to the present invention, can further comprise a substance useful in the treatment of a patient in need of peritoneal dialysis. Such a substance will be determined by the person of ordinary skill in this art, depending on the needs of the patient and his or her conditions, such as the presence of other pathological states of particular needs. Examples of such substance are: vitamins, optionally soluble vitamins, antioxidants and antifibrotic agents (such as N-substituted 2-(1H) pyridone(s) and/or N-substituted 3-(1H) pyridones.

In an embodiment, the solution has the following composition:

| | | |
|---|---|---|
| Xylitol mmol/l | 46 | (0.7% w/v) |
| Glucose mmol/l | 27.7 | (0.5% w/v) |
| L-Carnitine mmol/l | 1.24 | (0.02% w/v) |
| Sodium mmol/l | 132 | |
| Calcium mmol/l | 1.3 | |
| Magnesium mmol/l | 0.5 | |
| Chloride mmol/l | 103.5 | |
| Lactate mmol/l | 35 | |

In another embodiment, the solution has the following composition:

| | | |
|---|---|---|
| Xylitol mmol/l | 98.6 | (1.5% w/v) |
| Glucose mmol/l | 27.7 | (0.5% w/v) |
| L-Carnitine mmol/l | 1.24 | (0.02% w/v) |
| Sodium mmol/l | 132 | |
| Calcium mmol/l | 1.3 | |
| Magnesium mmol/l | 0.5 | |
| Chloride mmol/l | 103.5 | |
| Lactate mmol/l | 35 | |

In another embodiment, the solution has the following composition:

| | | |
|---|---|---|
| Xylitol mmol/l | 125 | (2.0% w/v) |
| Glucose mmol/l | 83 | (1.5% w/v) |
| L-Carnitine mmol/l | 1.24 | (0.02% w/v) |
| Sodium mmol/l | 132 | |
| Calcium mmol/l | 1.3 | |
| Magnesium mmol/l | 0.5 | |
| Chloride mmol/l | 103.5 | |
| Lactate mmol/l | 35 | |

In another embodiment, the solution has the following composition:

| | | |
|---|---|---|
| Xylitol mmol/l | 46 | (0.7% w/v) |
| Glucose mmol/l | 80.3 | (1.45% w/v) |
| L-Carnitine mmol/l | 1.24 | (0.02% w/v) |
| Sodium mmol/l | 132 | |
| Calcium mmol/l | 1.3 | |
| Magnesium mmol/l | 0.5 | |
| Chloride mmol/l | 103.5 | |
| Lactate mmol/l | 35 | |

In another embodiment, the solution has the following composition:

| | | |
|---|---|---|
| Xylitol mmol/l | 46 | (0.7% w/v) |
| Glucose mmol/l | 162 | (2.9% w/v) |
| L-Carnitine mmol/l | 1.24 | (0.02% w/v) |
| Sodium mmol/l | 132 | |
| Calcium mmol/l | 1.3 | |
| Magnesium mmol/l | 0.5 | |
| Chloride mmol/l | 103.5 | |
| Lactate mmol/l | 35 | |

In another embodiment, the solution has the following composition:

| | | |
|---|---|---|
| Xylitol mmol/l | 98.6 | (1.5% w/v) |
| Glucose mmol/l | 83 | (1.5% w/v) |
| L-Carnitine mmol/l | 1.24 | (0.02% w/v) |
| Sodium mmol/l | 132 | |
| Calcium mmol/l | 1.3 | |
| Magnesium mmol/l | 0.5 | |
| Chloride mmol/l | 103.5 | |
| Lactate mmol/l | 35 | |

In alternative embodiments, the solutions herein described are contained, stored and/or delivered in a bag. The bag can be single-, dual- or multi-chamber. Such bags are of common use in the field of peritoneal dialysis and available on the market.

In an embodiment, the solutions herein described are manufactured in single-chamber bags. Such bags are typically used for containing acid pH solutions.

In another embodiment, the solutions herein described are manufactured in double-chamber bags, typically PVC-free. The double-chamber bag is optionally used for neutral pH solutions, which are typically better tolerated by the subjects when administered into the peritoneal cavity. Said double-chamber bag is typically a large format bag containing 1+1 litre of solution, divided by a "weak seal" that ensures sterilization, storage, and transport of the bags while avoiding contacts between the two solutions. Mixing of the two solutions present in Compartment A and in Compartment B is easily carried out by the patient simply pressing on the weak seal, obtaining the final solution to be used for PD treatment. Such bags are of common use in the field and available on the market.

Therefore, in an embodiment the solution used in the present invention is obtained by the mixing of two solutions stored in two compartments of a double-chamber bag. In this embodiment, the composition of the solutions of the two compartments can be for example as follows:

| | Compart-ment A | | Compartment B | Compartment A + B (after reconstitution) | |
|---|---|---|---|---|---|
| Xylitol mmol/l | 92 | (1.4% w/v) | 0 | 46 | (0.7% w/v) |
| Glucose mmol/l | 55.4 | (1% w/v) | 0 | 27.7 | (0.5% w/v) |
| L-Carnitine mmol/l | 2.48 | (0.04% w/v) | 0 | 1.24 | (0.02% w/v) |
| Sodium mmol/l | 0 | | 264 | 132 | |
| Calcium mmol/l | 2.6 | | 0 | 1.3 | |
| Magnesium mmol/l | 1 | | 0 | 0.5 | |
| Chloride mmol/l | 0 | | 207 | 103.5 | |
| Lactate mmol/l | 0 | | 70 | 35 | |
| pH | 2.6-3.2 | | 8.0-8.5 | 7.1-7.4 | |
| Xylitol mmol/l | 197.2 | (3% w/v) | 0 | 98.6 | (1.5% w/v) |
| Glucose mmol/l | 55.4 | (1% w/v) | 0 | 27.7 | (0.5% w/v) |
| L-Carnitine mmol/l | 2.48 | (0.04% w/v) | 0 | 1.24 | (0.02% w/v) |
| Sodium mmol/l | 0 | | 264 | 132 | |
| Calcium mmol/l | 2.6 | | 0 | 1.3 | |
| Magnesium mmol/l | 1 | | 0 | 0.5 | |

-continued

|  | Compart-ment A | Compartment B | Compartment A + B (after reconstitution) |
|---|---|---|---|
| Chloride mmol/l | 0 | 207 | 103.5 |
| Lactate mmol/l | 0 | 70 | 35 |
| pH | 2.6-3.2 | 8.0-8.5 | 7.1-7.4 |
| Xylitol mmol/l | 250 (4% w/v) | 0 | 125 (2.0% w/v) |
| Glucose mmol/l | 166 (3% w/v) | 0 | 83 (1.5% w/v) |
| L-Carnitine mmol/l | 2.48 (0.04% w/v) | 0 | 1.24 (0.02% w/v) |
| Sodium mmol/l | 0 | 264 | 132 |
| Calcium mmol/l | 2.6 | 0 | 1.3 |
| Magnesium mmol/l | 1 | 0 | 0.5 |
| Chloride mmol/l | 0 | 207 | 103.5 |
| Lactate mmol/l | 0 | 70 | 35 |
| pH | 2.6-3.2 | 8.0-8.5 | 7.1-7.4 |
| Xylitol mmol/l | 92 (1.4% w/v) | 0 | 46 (0.7% w/v) |
| Glucose mmol/l | 160.6 (2.9% w/v) | 0 | 80.3 (1.45% w/v) |
| L-Carnitine mmol/l | 2.48 (0.04% w/v) | 0 | 1.24 (0.02% w/v) |
| Sodium mmol/l | 0 | 264 | 132 |
| Calcium mmol/l | 2.6 | 0 | 1.3 |
| Magnesium mmol/l | 1 | 0 | 0.5 |
| Chloride mmol/l | 0 | 207 | 103.5 |
| Lactate mmol/l | 0 | 70 | 35 |
| pH | 2.6-3.2 | 8.0-8.5 | 7.1-7.4 |
| Xylitol mmol/l | 92 (1.4% w/v) | 0 | 46 (0.7% w/v) |
| Glucose mmol/l | 324 (5.8% w/v) | 0 | 162 (2.9% w/V) |
| L-Carnitine mmol/l | 2.48 (0.04% w/v) | 0 | 1.24 (0.02% w/v) |
| Sodium mmol/l | 0 | 264 | 132 |
| Calcium mmol/l | 2.6 | 0 | 1.3 |
| Magnesium mmol/l | 1 | 0 | 0.5 |
| Chloride mmol/l | 0 | 207 | 103.5 |
| Lactate mmol/l | 0 | 70 | 35 |
| pH | 2.6-3.2 | 8.0-8.5 | 7.1-7.4 |
| Xylitol mmol/l | 92 (1.4% w/v) | 0 | 98.6 (1.5% w/v) |
| Glucose mmol/l | 166 (5.8% w/v) | 0 | 83 (1.5% w/v) |
| L-Carnitine mmol/l | 2.48 (0.04% w/v) | 0 | 1.24 (0.02% w/v) |
| Sodium mmol/l | 0 | 264 | 132 |
| Calcium mmol/l | 2.6 | 0 | 1.3 |
| Magnesium mmol/l | 1 | 0 | 0.5 |
| Chloride mmol/l | 0 | 207 | 103.5 |
| Lactate mmol/l | 0 | 70 | 35 |
| pH | 2.6-3.2 | 8.0-8.5 | 7.1-7.4 |

In all the above embodiments of solutions prepared in a double-compartment bag (Compartment A and Compartment B), pH may be adjusted, for example with excipients as 25% hydrochloric acid or sodium hydroxide in Compartment A, and sodium hydrogen carbonate in Compartment B. The skilled person knows how to perform these adjustments.

It has now been found that the above solution when used for peritoneal dialysis in subjects affected by end-stage renal disease and/or congestive heart failure is able to maintain or restore the ability of the subject to remove fluid and small solutes. In particular, the ability of the subject to remove solutes and fluids both from the peritoneal and kidney routes.

Indeed, patients responded to the treatment with the above solution with an improvement of both solutes and fluid removal both from the peritoneal and kidney routes.

Total weekly urea Kt/V ($Kt/V_{urea}$), weekly total creatinine clearance (CrCl), peritoneal Equilibrium Test creatinine (PET-Cr), Peritoneal Equilibrium Test glucose (PET-GI), and Residual Kidney Function (RKF) were used as parameters representative of the efficacy of depuration/removal of small molecules through the peritoneal membrane and kidney, whereas diuresis, daily ultrafiltration, and Peritoneal Equilibrium Test ultrafiltration (PET-UF) were used as parameters representative of the efficacy of fluid removal through the peritoneal membrane and kidney.

Taking into account all the above parameters, a clear trend in the improvement of small solutes and fluid removal was observed.

Furthermore, advantageously, all the patients responded with an increase of PET-Cr at the end of the treatment when compared to initial values and, contrary to what is expected according to the well-known Twardowsky profile of PET-Cr vs PET-GI, this was not associated with an equal increase of glucose absorption at all (See Peritoneal equilibration test. Zbylut j. Twardowski, Karl O. Nolph, Ramesh Khanna, Barbara F. Prowant, Leonor P. Ryan, Harold L. Moore, and Marc P. Nielsen. Perit Dial Int July/September 1987 7:138-148). Indeed, with the traditional glucose-based PD solution, an increase of PET-Cr is always associated with an increase of glucose absorption evaluated with PET-GI. This means that a reduced glucose absorption observed with the solution herein described sustains the osmotic gradient for longer period during the dwell, favoring both fluid and solute removal.

In addition, since both residual kidney function and residual diuresis were not affected by the treatment with the solutions herein described, the observed increase in fluid removal clearly indicate that volume control is not only maintained but improved.

Quality of life was used as a parameter representative of the overall status of patients' wellbeing and it was found that quality of life is not compromised by the treatment with the solutions herein described. This is particularly surprising and advantageous in consideration of the fact that the solutions were slightly acidic. Indeed, a solution with a neutral pH is usually better tolerated by PD patients (Cho Y, Johnson D W, Craig J C, Strippoli G F, Badve S V, Wiggins K J: Biocompatible dialysis fluids for peritoneal dialysis. Cochrane Database Syst Rev 3:CD007554, 2014).

In alternative embodiments, within the context of embodiments provided herein, for "maintaining the removal of small solutes and fluids" it is intended that in a subject undergoing a peritoneal dialysis treatment with the solution herein described the ability to remove small solutes and fluid remains almost the same as before starting the treatment. In some embodiments, said subject is a subject starting a peritoneal dialysis treatment, i.e. a subject who was not previously treated with peritoneal dialysis; such subject has a deficit in the ability to remove small solutes and fluid and this deficit remains almost the same before and after the treatment with the solutions herein described, so that the ability to remove small solutes and fluid is advantageously maintained according to the present invention. In other words, the subject undergoing peritoneal dialysis according to the present invention does not suffer the decay of clinical efficacy experienced with the glucose solutions known in the art. In other embodiments, the subject undergoing a peritoneal dialysis treatment with the solution herein described was previously treated with peritoneal dialysis solutions containing only glucose as osmotic agent and/or is a subject who already developed a kidney and/or peritoneal damage due to previous peritoneal dialysis treatment and/or has a residual kidney function compromised; such subject has a deficit in the ability to remove small solutes and fluid and this deficit remains almost the same before and after the treatment with the solutions herein described, so that the ability to remove small solutes and fluid advantageously does not get worse, i.e. is maintained.

In alternative embodiments, within the context of embodiments provided herein, for "restoring the removal of small solutes and fluids" it is intended that a subject undergoing a peritoneal dialysis treatment with the solutions herein described had a deficit in the ability to remove small solutes and fluid before starting the treatment with such solution and after the starting of the treatment the ability to remove small solutes and liquid is restored. In some embodiments, the subject undergoing a peritoneal dialysis treatment with the solution herein described was previously treated with peritoneal dialysis solutions containing only glucose as osmotic agent and/or is a subject who already developed a kidney and/or peritoneal damage due to previous peritoneal dialysis treatment and/or has a residual kidney function compromised; such subject has a deficit, even a severe one, in the ability to remove small solutes and fluid and this ability is advantageously restored after the treatment with the solutions herein described. In a preferred embodiment, said restoring means that the ability to remove small solutes and liquid improves with the treatment with respect to the condition present at the starting of the treatment. This improvement is a clinically acceptable improvement, i.e. an improvement in the clinical condition which would be considered acceptable from a person skilled in the field, such as a nephrologist.

In alternative embodiments, within the context of embodiments provided herein, when the solution is used for peritoneal dialysis in subjects suffering from congestive heart failure the definition peritoneal ultrafiltration may be used instead of peritoneal dialysis.

In alternative embodiments, within the context of embodiments provided herein, the use of this solution for peritoneal dialysis in subjects suffering from end-stage renal disease and/or congestive heart failure provides the advantage of maintaining or restoring the depurative efficacy and/or the ultrafiltration.

As mentioned above, this advantage has been shown in clinical trials in subjects undergoing peritoneal dialysis, wherein using the solution above described the depurative efficacy has been maintained or restored.

For depurative efficacy it is herein intended the ability in removing small solutes. In particular, it is the small solutes clearance.

In alternative embodiments, depurative efficacy is measured by the parameter total weekly $Kt/V_{urea}$. For the sake of simplicity $Kt/V_{urea}$ is herein indicated simply as $Kt/V$.

$Kt/V$ is a parameter commonly used to quantify peritoneal dialysis treatment adequacy, wherein:
K is urea clearance in mL/min,
t is time in minutes,
V is volume of distribution of urea.
V can be estimated or obtained by a numerical equation, such as the Watson equation.

For example, it can be estimated as the body water content, which is about 60% of the weight for males, 55% of the weight for females.

Also, V can be obtained with the following Watson equation:

V male (L): 2.447+0.3362×weight (KG)+0.1074× height (cm)−0.09516×age (year)

V female (L): −2.097+0.2466×weight (Kg)+0.1069× height (cm)

The skilled person in the field, such as a nephrologist, knows how to obtain the total weekly $Kt/V_{urea}$. Reference can be made for example to the work of Burkart J. M. Adequacy of peritoneal dialysis. In: Gokal R, Khannan R, Krediet R Th, Nolph K D (eds.), Textbook of Peritoneal Dialysis, 2nd edition, 465-497, 2000.

In another embodiment, depurative efficacy is measured by the parameter weekly total creatinine clearance, herein indicated also as CrCl. The skilled person in the field, such as a nephrologist, knows how to obtain the total weekly creatinine clearance. Reference can be made for example to the above mentioned work of Burkart J. M., 2000.

In an embodiment, depurative efficacy is measured by a combination of Kt/V and CrCl. The skilled person knows how to evaluate the depurative efficacy based on these parameters.

For maintaining depurative efficacy it is intended that depurative efficacy remains almost the same before and after the use of the solution herein described for peritoneal dialysis of a subject. In a particular embodiment, it means that the Kt/V remains in the range of 1.4-1.8.

For restoring depurative efficacy it is intended that in a subject having a deficit thereof depurative efficacy improves after the use of the solution herein described for peritoneal dialysis. In particular, it means that the Kt/V increases to a value of at least 1.5±0.1, optionally to a value comprised between 1.7±0.1 and 1.8±0.1.

In alternative embodiments, the use of the solution herein described for peritoneal dialysis in subjects suffering from end-stage renal disease and/or congestive heart failure provides the advantage of maintaining or restoring the peritoneal ultrafiltration.

For peritoneal ultrafiltration it is herein intended the ability of the subject to remove fluids from the peritoneum.

Ultrafiltration is herein used as synonym of peritoneal ultrafiltration.

Such ultrafiltration in a subject can be measured by the parameter of daily ultrafiltrate.

The skilled person in the field, such as a nephrologist, knows how to measure the ultrafiltration. As a reference see for example Nephrol Dial Transplant. 2010 July; 25(7): 2052-62. doi: 10.1093/ndt/gfq100. Evaluation of peritoneal membrane characteristics: clinical advice for prescription management by the ERBP working group. van Biesen W1, Heimburger O, Krediet R, Rippe B, La Milia V, Covic A, Vanholder R; ERBP working group on peritoneal dialysis.

For example, to calculate peritoneal ultrafiltration, at each dwell the fresh PD bag is weighed before and after the flush before fill procedure, to correct for the flush before fill rinsing volume (being not used a fixed volume) and for possible over-or underfill of the bag. From the latter weight, the volume of infused PD solution is obtained by subtracting the weight of the empty bag. The volume of the drained dialysate is measured by weighing the drainage bag and then subtracting the weight of the empty bag. Peritoneal ultrafiltration is calculated (mL) as drained (mL)–infused (mL) volume.

For "maintaining" ultrafiltration it is intended that ultrafiltration remains almost the same before and after the use of the solutions herein described for peritoneal dialysis in a subject. In particular, it means that the drained volume is maintained higher than the infused volume.

For "restoring" ultrafiltration it is intended that in a subject having a deficit thereof ultrafiltration improves after the use of the solutions herein described for peritoneal dialysis. In an embodiment, this means that the drained volume is restored higher than the infused volume.

The aim of maintaining or restoring ultrafiltration is to maintain or restore in the patient a condition of euvolemia. Therefore, in an embodiment, with the use of the solutions herein described it is maintained or restored in the subject a condition of euvolemia, which is evaluated according to clinical signs of volume overload, such as edema and increased blood pressure, and quality of life.

In an embodiment, ultrafiltration in a subject is measured by carrying out the Peritoneal Equilibrium Test ultrafiltration (PET-UF). This is a well-known test to evaluate the peritoneal membrane permeability. This test is also commonly used to evaluate the ultrafiltrative capacity of the peritoneal membrane by using a peritoneal dialysis solution having a high glucose concentration, such as 3.86%.

According to a further embodiment of the present invention, the use of the solutions herein described for peritoneal dialysis for the treatment of end-stage renal disease and/or of congestive heart failure results in an improvement of the removal of small solutes and fluids.

In particular, use of the solutions herein described for peritoneal dialysis results in an improvement of depurative efficacy and/or of ultrafiltration.

In a particular embodiment, the use of the solutions herein described for peritoneal dialysis results in an improvement of the depurative efficacy.

As mentioned above, the improvement of depurative efficacy can be evaluated by measurement of the Kt/V. In an embodiment, the improvement of depurative efficacy is an increase of the Kt/V.

In an embodiment, the Kt/V is measured at the beginning of the treatment with the solution herein described and after an adequate period of treatment. Such period is for example at least 28 days. It can also be more than 28 days, for example 1, 2, 3 or more months. An increase between the Kt/V measured at the beginning of the treatment and the Kt/V measured after a certain period of treatment is an indication of an improvement of depurative efficacy.

In an embodiment, the Kt/V of the subject before the treatment is lower than 1.7, optionally lower than 1.5.

The improvement of the depurative efficacy can be in particular with respect to the use of a equiosmolar solution for peritoneal dialysis containing as osmotic agent only glucose or other osmotic agents different from the combination of osmotic agents of the solution herein described. For example, such equiosmolar solution can be a commercial standard glucose solution such as PHYSIONEAL™, FIXIONEAL™, DIANEAL™ or DIANEAL LOW CALCIUM™, BALANCE™, BICAVERA™, BICANOVA™ or EQUIBALANCE™, having glucose at concentration of 1.36%, 1.5%, 2.27%, 2.5%, 3.86% or 4.25%. In this embodiment, the subject underwent a treatment with such equiosmolar solution before starting the treatment with the solution herein described. In a preferred embodiment, such subject who underwent a treatment with such equiosmolar solution already has a peritoneal and/or kidney damage.

In a particular embodiment, the use of the solutions herein described for peritoneal results in an improvement of ultrafiltration.

The improvement of ultrafiltration can be evaluated as described above.

In an embodiment, as above described in relation to the Kt/V parameter, the ultrafiltration is measured at the beginning of the treatment with the solution herein described and after an adequate period of treatment. Such period is for example at least 28 days. It can also be more than 28 days, for example 1, 2, 3 or more months.

The improvement of ultrafiltration can be in particular with respect to the use of a equiosmolar solution for peritoneal dialysis containing as osmotic agent only glucose or other osmotic agents different from the combination of osmotic agents of the solution herein described.

In an embodiment, the use of the solutions herein described for peritoneal dialysis allows to maintain or restore the removal of small solutes and fluid in the subject advantageously preserving at the same time the residual kidney function. The residual kidney function (RKF) is a parameter of common use in the field, typically evaluated according to the average renal clearances of urea and creatinine.

In an embodiment, the solution herein described is used in subjects wherein the ability of the kidney and/or of the peritoneal membrane of removing small solutes and fluids is not yet compromised. In particular, wherein the depurative efficacy and/or the ultrafiltration is acceptable. For example, in subjects having a Kt/V comprised between 1.4 and 1.7. In this embodiment, the solution is used for preventing the kidney and/or peritoneal damage, in particular for preventing a decrease in the ability of the subject of removing small solutes and fluids, at the same time preserving residual kidney function.

Indeed, it has been found that the use of the solutions herein described for peritoneal dialysis in subjects having an end-stage renal disease or congestive heart failure, in particular in subjects which never underwent a peritoneal dialysis treatment, is able to prevent the development of peritoneal damage, in particular to prevent the development of peritoneal fibrosis.

Fibrosis, angiogenesis and microvascular alteration are main pathogenetic mechanisms involved in the progressive loss of the peritoneal ultrafiltration capacity in patients undergoing peritoneal dialysis. Main cause of this condition is the continuous peritoneal exposure to hyperosmotic and hyperglycaemic agents. High glucose level activates the Mesothelial to Mesenchymal Transition (MMT) and the Endothelial-to-Mesenchymal (EndMT) program, which are responsible for the development of fibrosis/chronic peritoneal damage. Moreover, the high glucose content of PD solutions may induce the VEGF production with consequent neo-angiogenesis.

It has now been found that the solutions herein described have less pro-fibrotic potentials compared to conventional glucose-based solutions. Indeed, they have a better effect than glucose based solutions with comparable osmotic strength in terms of MMT/EndoMT event that sustain fibrosis but also apoptosis and angiogenesis, events which favors the loose of peritoneal filtration capacity. In particular, gene expression analysis of endothelial and mesothelial cells treated with solutions according to the present invention revealed a significant down-regulation of transcripts encoding for MMT/EndoMT biomarkers (SNAIL and α-SMA), apoptosis and angiogenesis compared to glucose solution with comparable osmotic strength.

Advantageously, it has been found that quality of life in subjects undergoing peritoneal dialysis with the solution herein described does not vary notwithstanding the slightly acidic pH of the solutions of the invention. A slightly acidic peritoneal dialysis solution is indeed believed to induce discomfort to the patient, as already mentioned above. Therefore, the use of the solutions herein described allows to improve the depurative efficacy and/or the ultrafiltration at the same time maintaining quality of life in the patients.

The solution for the use of the invention can be used for continuous ambulatory peritoneal dialysis (CAPD) or for automatic peritoneal dialysis (APD). Both are treatments well known in the field and the skilled person knows how to use the solutions herein described in those contexts. Optionally, the solution is for use for CAPD.

The solution herein described can be used for nocturnal exchange and/or for one or more diurnal exchanges. The skilled person knows what is intended for nocturnal and diurnal exchanges.

For example, when the solution is used for nocturnal exchange one bag containing the solution is used by the subject for the nocturnal cycle. When the solution is used for diurnal exchanges, one or more bags containing the solution are used by the subject for daily cycles.

In an embodiment, the solution is used for the nocturnal exchange and has the following composition: 1.5% w/v xylitol, 0.5% w/v glucose and 0.02% w/v L-carnitine.

In an embodiment, the solution is used for one or more, optionally 1, 2 or 3 diurnal exchanges and has the following composition: 0.7% w/v xylitol, 0.5% w/v glucose and 0.02% w/v L-carnitine. In this embodiment, the use of the solution for the diurnal exchanges can be combined with the use of a solution for peritoneal dialysis containing icodextrin for the nocturnal exchange. Such solutions containing icodextrin are commercially available and of common use in the field. An example of such commercial solution is Extraneal, comprising 7.5% icodextrin.

The skilled person, such as a nephrologist, knows how to use the solutions for the herein disclosed uses in clinical practice according to general knowledge in the field. Reference can be made, for example to the Textbook of Peritoneal Dialysis, second edition, Gokal R, Khanna R, Krediet R, Nolph K (Editors). Kluwer Academic Publishers, 2000.

According to the present invention the solutions herein described are for use for the treatment of end-stage renal disease (ESRD) and/or congestive heart failure.

End-stage renal disease (ESRD), also named kidney failure, is the last stage of chronic kidney disease, wherein dialysis is necessary.

In an embodiment of the invention, the solution is used in a subject affected by ESRD. Such subject can be for example a subject who never underwent peritoneal dialysis or it can be a subject already treated with peritoneal dialysis. Therefore, it can be a subject in which the condition of the residual kidney function and/or of the peritoneal membrane is only slightly compromised or is compromised or is highly compromised.

In alternative embodiments, the subject affected by ESRD is stable, wherein for stable it is intended hat he/she has a stable clinical condition. In a further preferred embodiment, the subject affected by ESRD does not have major cardiovascular co-morbidities. Optionally, the subject was previously treated for at least one month with a solution containing glucose for diurnal or nocturnal dwells. In a preferred embodiment, the subject was treated for at least three months with a solution containing glucose, optionally 2.5% of glucose, for the nocturnal dwell. In another preferred embodiment, the subject was previously treated for at least one month with 1, 2 or 3 diurnal exchange bag solutions containing glucose, optionally 1.5% glucose, combined with a nocturnal exchange with icodextrin, optionally a solution containing 7.5% icodextrin.

In another embodiment, the solution is used in a subject affected by congestive heart failure.

For congestive heart failure it is intended a condition wherein the heart is unable to pump sufficiently to maintain blood flow to meet the body's needs. In a preferred embodiment, the subject is affected by severe congestive heart failure resistant to diuretic therapy.

In an embodiment, the solution is used in a subject affected by both ESRD and congestive heart failure.

The solution for peritoneal dialysis herein disclosed can be included in a package for peritoneal dialysis. A package for peritoneal dialysis is a set of supplies for executing one or more cycles of peritoneal dialysis. A package can contain, for example one or more bags containing the peritoneal dialysis solution of the present invention, even with different formulations, for example for day and/or night cycles. Additional supplies/equipment can be present, such as a disposable connector for executing the peritoneal dialysis cycle. Examples of packages are those commonly marketed.

The solutions herein disclosed can be delivered ready-to-use to the subject in need thereof or prepared at the time of use. In the latter circumstance, the solution can be prepared at home by the subject in need of peritoneal dialysis beginning with a source of purified water and adding the ingredients composing the solution, for example from one or more concentrates or powders, in order to obtain the fluid for peritoneal dialysis with the desired concentration of each ingredient. A peritoneal dialysis home machine can be used for this purpose. All such procedures and apparatus for self-preparing peritoneal dialysis solutions are known in the art, see for example Automated peritoneal dialysis with 'on-line'-prepared bicarbonate-buffered dialysate: technique and first clinical experiences (Brunkhorst R, Fromm S, Wrenger E, Berke A, Petersen R, Riede G, Westphale J, Zamore E, Ledebo I. Nephrol Dial Transplant. 1998 December; 13(12):3189-92) and On-line preparation of solutions for dialysis: practical aspects versus safety and regulations (Ledebo I. J Am Soc Nephrol. 2002 January; 13 Suppl 1:S78-83).

It is an object of the invention the solution for the use of the invention in the form of a concentrate or a powder, in particular to be used in a peritoneal dialysis home machine.

In an embodiment, the solution is in the form of a concentrate. Optionally, said concentrate comprises each of the osmotic ingredients, i.e., xylitol, carnitine, glucose, glycerol, polydextrin, in a concentration 2 to 10 fold the concentration of the osmotic agent in the final solution. For example, the osmotic agents may be provided as single bags containing the single osmotic ingredient at a concentration 2 to 10 fold its final concentration in the solution to be administered to the patient. A package comprising such bags for the administration in the methods herein disclosed is within the scope of the present invention. The concentrate solution may be present in sterile water or in sterile water containing salts and buffers present at a concentration ready to be administered to the patient. In another embodiment, a concentrated solution contains fix combination of the osmotic ingredients, such as xylitol-glucose-carnitine, xylitol-glucose-carnitine-glycerol, xylitol-polydextrin-carnitine, in a bag whereby their concentration is 2 to 10 fold of their final concentration in the solution to be administered to the patient. A package comprising such bag for the administration in the methods herein disclosed is within the scope of the present invention. The concentrate solution may be present in sterile water or in sterile water containing salts and buffers present at a concentration ready to be administered to the patient. The content of these concentrated bags will be diluted with locally prepared water with reverse osmosis, as it is done in hemodialysis done both at home or in dialysis centers. The mixing and delivery of the final solution to the patient is done with a dialysis machine whose principle are well known by the experts in the field of peritoneal dialysis and hemodialysis.

In an embodiment, the solution is in a dry form, i.e. in the form of a powder. The osmotic ingredients either alone or according to the fix combinations reported in the various embodiments reported above can be prepared in a cartridge containing such ingredients in the dry form of a powder. A package comprising such cartridge for the administration in the methods herein disclosed is within the scope of the present invention. These cartridges also contain the necessary salts and buffer, as described in the various embodiments reported above. This kind of forms are of common use in the field of haemodialysis for the preparation of dialysis fluids. The content of the cartridges will be diluted with locally prepared water with reverse osmosis, as it is done in hemodialysis done both at home or in dialysis centers. The mixing and delivery of the final solution to the patient is done with a dialysis machine whose principle are well known by the experts in the field of peritoneal dialysis and hemodialysis.

In alternative embodiments, the solution named polycore (1.5% w/v xylitol, 4.0 w/v polydextrin and 0.02% w/v carnitine) is administered to a subject affected by congestive heart failure, wherein for congestive heart failure it is intended a condition wherein the heart is unable to pump sufficiently to maintain blood flow to meet the body's needs. Optionally the subject affected by severe congestive heart failure is also resistant to diuretic therapy. The the solution named polycore (1.5% w/v xylitol, 4.0 w/v polydextrin and 0.02% w/v carnitine) is administered by peritoneal dialysis or peritoneal ultrafiltration to the subject affected by severe congestive heart failure. Wherein the subject affected by severe congestive heart failure, may be characterised by the following symptoms and clinical parameters:

1. Heart Failure with left ventricular ejection fraction 560%, and
2. Heart Failure symptoms consistent with NYHA Classification of III-IV despite guidelines directed medical therapy (GDMT), and
3. Persistency of right ventricular failure due to after load mismatch as addressed by the presence of disproportioned increase of the right atrial pressure (RAP) versus the capillary wedge pressure (CWP) with a ratio >0.65 detected with right heart catheterization performed after stable GDMT and comprehensive of loop diuretic (furosemide) oral dose till to 2.0 mg/kg/day, coupled with urinary sodium excretion ≤65 mEq/day, confirmatory of loop diuretic resistance. Despite absence of urinary sodium excretion ≤65 mEq/day, the late persistence (till to 30 days) of pulmonary or systemic congestion in HF patients managed with GDMT, including furosemide oral dose till to 2.0 mg/kg/day, and
4. decreased kidney function addressed by the measured GFR, defined as (urea clearance+creatinine clearance)/2 between 15 and 60 ml/min/1.73 m$^2$.

The details of one or more exemplary embodiments of the invention are set forth in the description above. Other features, objects, and advantages of the invention will be apparent from the description, and from the claims.

All publications, patents, patent applications cited herein are hereby expressly incorporated by reference in their entireties for all purposes.

Any of the above aspects and embodiments can be combined with any other aspect or embodiment as disclosed here in the Summary, Figures and/or Detailed Description sections.

As used in this specification and the claims, the singular forms "a," "an" and "the" include plural referents unless the context clearly dictates otherwise.

Unless specifically stated or obvious from context, as used herein, the term "or" is understood to be inclusive and covers both "or" and "and".

Unless specifically stated or obvious from context, as used herein, the term "about" is understood as within a range of normal tolerance in the art, for example within 2 standard deviations of the mean. About can be understood as within 20%, 19%, 18%, 17%, 16%, 15%, 14%, 13%, 12% 11%, 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Unless specifically stated or obvious from context, as used herein, the terms "substantially all", "substantially most of", "substantially all of" or "majority of" encompass at least about 90%, 95%, 97%, 98%, 99% or 99.5%, or more of a referenced amount of a composition.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents. Incorporation by reference of these documents, standing alone, should not be construed as an assertion or admission that any portion of the contents of any document is considered to be essential material for satisfying any national or regional statutory disclosure requirement for patent applications. Notwithstanding, the right is reserved for relying upon any of such documents, where appropriate, for providing material deemed essential to the claimed subject matter by an examining authority or court.

Modifications may be made to the foregoing without departing from the basic aspects of the invention. Although the invention has been described in substantial detail with reference to one or more specific embodiments, those of ordinary skill in the art will recognize that changes may be made to the embodiments specifically disclosed in this application, and yet these modifications and improvements are within the scope and spirit of the invention. The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. Thus, the terms and expressions which have been employed are used as terms of description and not of limitation, equivalents of the features shown and described, or portions thereof, are not excluded, and it is recognized that various modifications are possible within the scope of the invention. Embodiments of the invention are set forth in the following claims.

The invention will be further described with reference to the examples described herein; however, it is to be understood that the invention is not limited to such examples.

EXAMPLES

Example 1

Efficacy and Safety Assessments of a Peritoneal Dialysis Solution Containing Glucose, Xylitol and L-Carnitine Compared to Standard PD Solutions in Continuous Ambulatory Peritoneal Dialysis (CAPD)

1. Aim of the Study

The aim of this study was to evaluate:
1) the effects of an exemplary solution according to the present invention, herein named IPX15, containing xylitol (1.5%), glucose (0.5%), and L-carnitine (0.02%) as osmotic agents comparable to the standard 2.5% glucose PD solution, for the nocturnal exchange in 20 ESRD patients on Continuous Ambulatory Peritoneal Dialysis (CAPD) (Group A)
and
2) the effects of an exemplary solution according to the present invention, herein named IPX07, containing xylitol (0.7%), glucose (0.5%) and L-Carnitine (0.02%) as osmotic agents comparable to the standard 1.5% glucose PD solution, for diurnal exchanges (1, 2 or 3 exchanges), combined with icodextrin for the nocturnal dwell, in 20 ESRD patients on Continuous Ambulatory Peritoneal Dialysis (CAPD) (Group B)

2. Study Plan 2.1 Screening Period

The eligible patients were assigned to Group A or Group B and entered a 4 weeks run-in period (screening period), dedicated to the identification of eligible subjects, after having understood the study aims and signed a written informed consent.

During the screening period, Group A received standard solution with 2.27% glucose for the nocturnal exchange and Group B received their standard PD therapy (1, 2 or 3 diurnal exchanges with standard solution with 1.36% glucose and one nocturnal exchange bag solution with 7.5% icodextrin (Extraneal)).

2.2 Intervention Period

The intervention period lasted for 4 weeks.

The subjects included in the Group A received a bag with experimental solution IPX15 for the nocturnal dwell.

The subjects included in the Group B received 1, 2 or 3 bags with the experimental solution IPX07 for the daily exchanges and a bag with icodextrin solution for the nocturnal dwell.

All subjects went to the Center to undergo study visits. At each visit, the Investigator performed clinical and laboratory assessments, according to the study flow chart. The patient compliance to treatment, changes in concomitant diseases and medications, and adverse events occurrence were recorded.

3. Target Study Population

Stable, End-Stage Renal Disease (ESRD) patients on Continuous Ambulatory Peritoneal Dialysis (CAPD) without major cardiovascular comorbidities, regularly treated for at least three months before selection with a standard solution containing 2.5% of glucose for the nocturnal dwell (Group A) or regularly treated for at least one month before selection with 1, 2 or 3 diurnal exchange bag solution containing 1.5% glucose combined with a nocturnal exchange with Extraneal (Group B), were investigated.

4. Treatment Procedures 4.1 Treatment During the Study

The experimental solution used in this study was produced in accordance with Good Manufacturing Practice (GMP) by Ind. Farmaceutica Galenica Senese S.r.l., Via Cassia Nord 351-53104 Monteroni d'Arbia (SI) Italy.

Two different experimental solution bags were used:
Product code IPX15: the formulation comprises bag with sterile solution for peritoneal dialysis containing xylitol (1.5%), glucose (0.5%), and L-Carnitine (0.02%) to be used in the Group A treated with the experimental solution bag during the nocturnal exchange;
Product code IPX07: the formulation comprises bag with sterile solution for peritoneal dialysis containing xylitol (0.7%), glucose (0.5%), and L-Carnitine (0.02%) to be used in the Group B treated with the experimental solution bags during the 1, 2 or 3 diurnal exchanges.

Table 1 below reports the complete composition of the two solutions.

TABLE 1

| Xylocore composition | | |
|---|---|---|
| Product code | IPX07 | IPX15 |
| Osmotic Strenght | Low Strenght | Medium Strenght |
| Xylitol mmol/l | 46 (0.7% w/v) | 98.6 (1.5% w/v) |
| Glucose mmol/l | 27.7 (0.5% w/v) | |
| L-Carnitine mmol/l | 1.24 (0.02% w/v) | |
| Sodium mmol/l | 132 | |
| Calcium mmol/l | 1.3 | |
| Magnesium mmol/l | 0.5 | |
| Chloride mmol/l | 103.5 | |
| Lactate mmol/l | 35 | |
| pH | 5.5 +/− 0.5 | |
| osmolarity mosmol/l | 349 | 401 |

4.2 Dosage, Schedule and Administration of Investigational Product

During the 4-weeks Intervention Period patients were treated according to the following schedule:
GROUP A: the bag with experimental solution with product code IPX15 was used for the nocturnal exchange;
GROUP B: the bag with experimental solution with product code IPX07 was used for the diurnal exchanges (1, 2 or 3), while a bag with 7.5% icodextrin solution was used for the nocturnal exchange.

5. Efficacy Assessment 5.1 Efficacy Parameters

The following efficacy parameters were assessed during the study:
1. Total weekly urea KtN (Kt/V);
2. Weekly total creatinine clearance (CrCL);
3 Peritoneal Equilibrium Test creatinine (PET-Cr);

4. Peritoneal Equilibrium Test glucose (PET-Gl)
5. Residual Kidney Function evaluated according to the average renal clearances of Urea and Creatinine (RKF);
6. Residual daily diuresis (Diuresis);
7. Daily ultrafiltration (Daily UF);
8. Peritoneal Equilibrium Test ultrafiltration (PET-UF);
9. Quality of Life (QoL).

All these functional parameters were performed according to the standard clinical procedures (Burkart J. M., 2000), whereas for the QoL, a modified version of the questionnaire SF-12 on the patient's perception of well-being has been administered to PD patients (Eduardo Lacson, Jianglin Xu, Shu-Fang Lin, Sandie Guerra Dean, J. Michael Lazarus and Raymond M. Hakim. A Comparison of SF-36 and SF-12 Composite Scores and Subsequent Hospitalization and Mortality Risks in Long-Term Dialysis Patients. CJASN February 2010, 5 (2) 252-260).

Statistical Analysis

For each clinical parameter, the difference between day 28 and day 0 was calculated from which the percentage of positive and negative responses, for each patient, was obtained. Finally the average of the positive and negative responses was calculated.

In order to assess whether these two averages were equivalent, in the presence of a small sample, with non-independent data, it was decided to use the Wilcoxon Signed Rank-Sum test, a non-parametric type test that does not presuppose any type of distribution underlying the data.

Results

As described above, the patients were divided in two groups, A and B, with the following treatments:

Control (Time 0)
Group A: one long-dwell with PHYSIONEAL™ 2.27% Glucose—no diurnal exchanges
Group B: one long-dwell with 7.5% Icodextrin plus 1 or 2 short-dwell exchanged with PHYSIONEAL™ 1.36% Glucose (Baxter)

Control (Time 28 days)
Group A: one long-dwell with experimental solution with product code IPX15 (osmotic strenght equivalent to PHYSIONEAL™ 2.27% glucose), no diurnal exchanges
Group B: one long-dwell with 7.5% Icodextrin (Baxter) plus 1 or 2 short-dwell exchanged with experimental solution with product code IPX07 (osmotic strength equivalent to PHYSIONEAL™ 1.36% Glucose—Baxter)

Though the two groups of patients had some differences in the PD schedule (number and daytime of PD exchanges) and in the PD solution prescription (icodextrin in group B only), they were combined in the statistical analysis since in all PD patients, regardless of the above differences, the primary target is removal of both fluid and solutes.

The Tables 2-4 below report the results of the study, as explained hereinafter.

TABLE 2

Listing of patients with observed values at day 0, 28 and changes [day 28 − day 0]

| | Kt/V | | | Tot. clear. creat. | | | PET creat. (PET-Cr) | | | PET glucosio (PET-Gl) | | |
|---|---|---|---|---|---|---|---|---|---|---|---|---|
| | Time | | | Time | | | Time | | | Time | | |
| | 0 | 28 | Delta | 0 | 28 | Delta | 0 | 28 | Delta | 0 | 28 | Delta |
| 1 | 1.24 | 1.08 | −0.16 | 50.03 | 42.38 | −7.65 | 0.68 | 0.75 | 0.07 | 0.31 | 0.28 | −0.03 |
| 2 | 1.10 | 1.07 | −0.03 | 78.04 | 55.45 | −22.59 | 0.67 | 0.82 | 0.15 | 0.24 | 0.22 | −0.02 |
| 3 | 1.68 | 1.70 | 0.02 | 93.39 | 105.74 | 12.35 | 0.63 | 0.73 | 0.10 | 0.27 | 0.27 | 0.00 |
| 4 | 1.52 | 1.57 | 0.05 | 77.76 | 79.55 | 1.79 | 0.57 | 0.68 | 0.11 | 0.32 | 0.27 | −0.05 |
| 5 | 1.43 | 1.42 | −0.01 | 85.52 | 95.78 | 10.26 | 0.48 | 0.62 | 0.14 | 0.23 | 0.28 | 0.05 |
| 6 | 1.12 | 1.42 | 0.30 | 55.46 | 80.25 | 24.79 | 0.58 | 0.68 | 0.10 | 0.37 | 0.31 | −0.06 |
| 7 | 0.76 | 1.52 | 0.76 | 61.46 | 69.88 | 8.42 | 0.66 | 0.84 | 0.18 | 0.18 | 0.23 | 0.05 |
| 8 | 1.59 | 1.75 | 0.16 | 86.94 | 98.15 | 11.21 | 0.59 | 0.73 | 0.14 | 0.23 | 0.34 | 0.05 |
| 9 | 1.45 | 1.54 | 0.09 | 72.22 | 65.83 | −6.39 | 0.61 | 0.76 | 0.15 | 0.27 | 0.30 | 0.03 |
| 10 | 1.36 | 1.47 | 0.11 | 62.62 | 65.66 | 3.04 | 0.53 | 0.64 | 0.11 | 0.34 | 0.32 | −0.02 |

| | RKF (Aver.clear.U-Cr) | | | Diuresis | | | Daily UF (24 hrs) | | | PET UF | | |
|---|---|---|---|---|---|---|---|---|---|---|---|---|
| | Time | | | Time | | | Time | | | Time | | |
| | 0 | 28 | Delta | 0 | 28 | Delta | 0 | 28 | Delta | 0 | 28 | Delta |
| 1 | 4.99 | 4.23 | −0.76 | 1250 | 1100 | −150 | 0 | 200 | 200 | 500 | 200 | −300 |
| 2 | 7.72 | 5.48 | −2.24 | 1100 | 1500 | 400 | 0 | 100 | 100 | 500 | 500 | 0 |
| 3 | 9.24 | 10.46 | 1.22 | 1600 | 1500 | −100 | 100 | 100 | 0 | 300 | 500 | 200 |
| 4 | 7.79 | 7.97 | 0.18 | 2000 | 2300 | 300 | 300 | 200 | −100 | 750 | 750 | 0 |
| 5 | . | . | . | 1100 | 1100 | 0 | 250 | 300 | 50 | 1100 | 700 | −400 |
| 6 | 9.13 | 10.20 | 1.07 | 2700 | 2250 | −450 | 300 | 300 | 0 | 250 | 600 | 350 |
| 7 | 6.08 | 6.91 | 0.83 | 2100| | 2000 | −100 | 400 | 350 | −50 | 300 | 500 | 200 |
| 8 | 8.50 | 9.71 | 1.11 | 2200 | 2500 | 300 | 400 | 850 | 450 | 500 | 750 | 250 |
| 9 | 7.14 | 6.51 | −0.63 | 2100 | 1250 | −850 | 300 | 300 | 0 | 500 | 750 | 250 |
| 10 | 6.12 | 6.41 | 0.29 | 1750 | 1900 | 150 | 300 | 300 | 0 | 850 | 800 | −50 |

TABLE 2-continued

Listing of patients with observed values at day 0, 28 and changes [day 28 − day 0]

| | QoL | | |
|---|---|---|---|
| | Time | | |
| | 0 | 28 | Delta |
| 1 | 14 | 19 | 5 |
| 2 | 25 | 18 | −7 |
| 3 | 22 | 18 | −4 |
| 4 | 17 | 21 | 4 |
| 5 | . | . | . |
| 6 | 16 | 17 | 1 |
| 7 | 15 | 15 | 0 |
| 8 | 15 | 15 | 0 |
| 9 | 17 | 20 | 3 |
| 10 | 17 | 16 | −1 |

TABLE 3

Summary of observed values at day 0, day 28 and change [day 28 − day 0]

| Variable | N | Mean | Std Dev | 95% Conf. Interv. Lower | 95% Conf. Interv. Upper | Coeff. of Variation |
|---|---|---|---|---|---|---|
| Total Weekly Urea Kt/V (Kt/V) | | | | | | |
| Time0 | 10 | 1.325 | 0.275 | 1.128 | 1.521 | 20.764 |
| Time28 | 10 | 1.454 | 0.226 | 1.291 | 1.616 | 15.603 |
| Delta | 10 | 0.129 | 0.253 | −0.052 | 0.310 | 196.193 |
| Weekly Total Creatinine clearance (CrCl) | | | | | | |
| Time0 | 10 | 72.344 | 14.481 | 61.985 | 82.703 | 20.017 |
| Time28 | 10 | 75.867 | 19.992 | 61.565 | 90.169 | 26.352 |
| Delta | 10 | 3.523 | 13.195 | −5.916 | 12.962 | 374.529 |
| PET creatinine (PET-Cr) | | | | | | |
| Time0 | 10 | 0.600 | 0.063 | 0.554 | 0.645 | 10.628 |
| Time28 | 10 | 0.725 | 0.071 | 0.673 | 0.776 | 9.909 |
| Delta | 10 | 0.125 | 0.032 | 0.101 | 0.148 | 25.922 |
| PET glucose (PET-Gl) | | | | | | |
| Time0 | 10 | 0.282 | 0.056 | 0.242 | 0.322 | 19.976 |
| Time28 | 10 | 0.282 | 0.037 | 0.255 | 0.309 | 13.352 |
| Dalta | 10 | 8.327E-18 | 0.042 | −0.030 | 0.030 | 5.095E17 |
| Residual Kidney Function (RKF) | | | | | | |
| Time0 | 9 | 7.423 | 1.471 | 6.292 | 8.554 | 19.823 |
| Time28 | 9 | 7.542 | 2.191 | 5.857 | 9.226 | 29.059 |
| Delta | 9 | 0.119 | 1.147 | −0.763 | 1.001 | 965.261 |
| Diuresis | | | | | | |
| Time0 | 10 | 1790.000 | 528.519 | 141 | 216 | 29.526 |
| Tima28 | 10 | 1740.000 | 518.437 | 136 | 211 | 29.795 |
| Delta | 10 | −50.000 | 380.788 | −322.399 | 222.399 | −761.577 |
| Daily Ultrafiltration (Daily UF) | | | | | | |
| Time0 | 10 | 235.000 | 149.164 | 128.294 | 341.705 | 63.474 |
| Time28 | 10 | 300.000 | 212.132 | 148.249 | 451.750 | 70.710 |
| Delta | 10 | 65.000 | 158.201 | −48.170 | 178.170 | 243.387 |
| PET Ultrafiltration (PET-UF) | | | | | | |
| Time0 | 10 | 555.000 | 270.236 | 361.684 | 748.315 | 48.691 |
| Time28 | 10 | 605.000 | 184.767 | 472.825 | 737.174 | 30.540 |
| Delta | 10 | 50.000 | 248.327 | −127.642 | 227.642 | 496.655 |
| Quality of life (QoL) | | | | | | |
| Time0 | 9 | 17.556 | 3.609 | 14.781 | 20.329 | 20.559 |
| Time28 | 9 | 17.667 | 2.121 | 16.036 | 19.297 | 12.007 |
| Delta | 9 | 0.111 | 3.822 | −2.827 | 3.049 | 344 |

TABLE 4

Listing of patients with percentage of positive/negative response

| Obs | IdPat | Positive | Negative | Positive Mean | SD | Median | Signed rank p-value |
|---|---|---|---|---|---|---|---|
| 1 | 1 | 33 | 67 | 69.4 | 18.9 | 74.5 | 0.0156 |
| 2 | 2 | 44 | 56 | | | | |
| 3 | 3 | 78 | 22 | | | | |
| 4 | 4 | 78 | 22 | | | | |
| 5 | 5 | 71 | 29 | | | | |
| 6 | 6 | 78 | 22 | | | | |
| 7 | 7 | 78 | 22 | | | | |
| 8 | 8 | 100 | 0 | | | | |
| 9 | 9 | 67 | 33 | | | | |
| 10 | 10 | 67 | 33 | | | | |

Table 2 show the values of $Kt/V_{urea}$, CrCl, PET-Cr, PET-Gl, RKF, Diuresis, daily UF, PET-UF, and quality of life score measured in each patients coded as 1 to 10 at the beginning of the clinical trial and 28 days after the treatment with our experimental PD solutions.

Table 3 shows the mean±SD, 95% Conf. Interv. and Coeff. of variations of the parameters shown in Table 2.

Tables 2 and 3 also show the difference indicated as Delta between the single values measured at the end (T28) minus the values at the beginning of the treatment for each patient.

$Kt/V_{urea}$, CrCl, PET-Cr, PET-Gl, and RKF are representative of the efficacy of depuration/removal of small molecules through the peritoneal membrane and kidney, whereas Diuresis, daily UF, and PET-UF are representative of the efficacy of fluid removal through the peritoneal membrane and kidney.

QoL is shown in Tables 2 and 3 and is representative of the overall status of patients' wellbeing.

The majority of the patients responded to the treatment with an increase of the Delta value, which, irrespective of the extent of the differential changes, shows an improvement of both depuration and fluid removal both from the peritoneal and kidney routes.

In the case of solute removal, this is particularly evident for Kt/V, CrCl, and PET-Cr (Tables 2 and 3).

Likewise, a clear trend in the improvement of fluid removal is observed in the Daily-Uf after 28 days of treatment with our PD solution compared with the beginning of the clinical trial (Tables 2 and 3).

This finding was further corroborated by the increase of the ultrafiltration collected after the PET-Uf in the PD patients treated with our experimental PD solutions (Tables 2 and 3).

In addition, all the patients responded with an increase of PET-Cr at the end of the treatment when compared to initial values and, contrary to what is expected according to the well-known Twardowsky profile of PET-Cr vs PET-GI, this was not associated with an equal increase of glucose absorption in all patients (PET-GI values at the end vs the beginning of the treatment) (See Peritoneal equilibration test. Zbylut j. Twardowski, Karl O. Nolph, Ramesh Khanna, Barbara F. Prowant, Leonor P. Ryan, Harold L. Moore, and Marc P. Nielsen. Perit Dial Int Jul./Sep. 1987 7:138-148). Indeed, with the traditional glucose-based PD solution, an increase of PET-Cr is always associated with an increase of glucose absorption evaluated with PET-GI. This means that a reduced glucose absorption observed with PD solution sustains the osmotic gradient for longer period during the dwell, favoring both fluid and solute removal.

According to the most recent guidelines from the International Society of Peritoneal Dialysis and current clinical practices, dialytic prescription should take into account all the possible parameters describing both removal of solutes and fluids along with QoL (International comparison of peritoneal dialysis prescriptions from the Peritoneal Dialysis Outcomes and Practice Patterns Study (PDOPPS). Wang A Y, Zhao J, Bieber B, Kanjanabuch T, Wilkie M, Marshall M R, Kawanishi H, Perl J, Davies S; PDOPPS Dialysis Prescription and Fluid Management Working Group. Perit Dial Int. 2020 Jan. 17:896860819895356).

Therefore, we decided to analyze our findings by using a statistical analysis capable to take all these parameters as a whole to assess if the changes observed before and after the treatment period were casually driven or not.

As discussed above, since an increase of the measured value at the end of the treatment (Time 28) compared to the beginning of the study (Time 0) is believed to be beneficial for any of the parameter reported in Tables 2 and 3, the statistical analysis was conducted accordingly. Therefore, through the Wilcoxon Rank-Sum test, we observed a probability value on casuality (p-value=0.0156) which seems to suggest, in our sample, that the different percentage of positive responses compared to that of negative responses is not due to random effect but to a systematic effect (Table 4).

Conclusion

Taken together the results of the clinical trial indicate a significant improvement of dialytic treatment in PD patients exposed for 4 weeks to our PD experimental solutions.

Indeed, the parameters evaluated in this study are conventionally used to evaluate depuration efficacy (Kt/Vurea, CrCl, PET-Cr, PET-GI, and RKF) and fluid removal (Diuresis, daily UF, and PET-UF).

In addition, since both residual kidney function and residual diuresis were not affected by the treatment with our PD solutions, the observed increase in fluid removal clearly indicate that volume control is not only maintained but most likely improved.

As reported by the most recent guidelines of the ISPD, indeed, "High-quality PD prescription should aim to achieve and maintain clinical euvolemia while taking residual kidney function and its preservation into account, so that both fluid removal from peritoneal ultrafiltration and urine output are considered and residual kidney function is not compromised" (Perit Dial Int. 2020 Jan. 17:896860819895365. Volume management as a key dimension of a high-quality PD prescription. Wang A Y, Dong J, Xu X, Davies S.; International comparison of peritoneal dialysis prescriptions from the Peritoneal Dialysis Outcomes and Practice Patterns Study (PDOPPS). Wang A Y, Zhao J, Bieber B, Kanjanabuch T, Wilkie M, Marshall M R, Kawanishi H, Perl J, Davies S; PDOPPS Dialysis Prescription and Fluid Management Working Group. Perit Dial Int. 2020 Jan. 17:896860819895356).

Moreover, the observation that the quality of life score was not compromised by the treatment with our experimental PD solution should be evaluated in consideration of the fact that our acidic PD solutions (pH 5.5) replaced for 4 weeks the conventional glucose-based PD solution (PHYSIONEAL™) whose pH is neutral. It is believed that a PD solution with a neutral pH is better tolerated by PD patients (i.e., less discomfort or infusion pain after the instillation into the peritoneal cavity) (Cho Y, Johnson D W, Craig J C, Strippoli G F, Badve S V, Wiggins K J: Biocompatible dialysis fluids for peritoneal dialysis. Cochrane Database Syst Rev 3:CD007554, 2014).

The clinical parameters have a non-random statistical trend which leads us to believe that there is a statistically significant treatment effect when our PD solution is used in PD therapy.

Example 2

Peritoneal Dialysis Solution Containing Glucose, Xylitol and L-Carnitine Mitigated In Vitro Mesothelial and Endothelial to Mesenchymal Transition Fibrosis, angiogenesis and microvascular alteration are main pathogenetic mechanisms involved in the progressive loss of the peritoneal ultrafiltration capacity in patients undergoing peritoneal dialysis (PD).

Main cause of this condition is the continuous peritoneal exposure to hyperosmotic and hyperglycaemic agents. High glucose level activates the Mesothelial to Mesenchymal Transition (MMT) and the Endothelial-to-Mesenchymal (EndMT) program, which are responsible for the development of fibrosis/chronic peritoneal damage. Moreover, the high glucose content of PD solution may induce the VEGF production with consequent neo-angiogenesis. Therefore, the introduction of more biocompatible solutions in clinical practice is necessary for preserving the long-term peritoneal membrane. To this purpose we tested the in vitro effects of a PD solution according to the invention, at comparable osmotic strength (XyloCore).

Methods

Cell Culture and Treatments

Human peritoneal mesothelial cells (HMrSV5) were cultured in DMEM/F12 supplemented with 10% (v/v) heat-inactivated fetal bovine serum and 100 U/mL penicillin/streptomycin (Invitrogen) and growth in type I collagen coated plastics. HMVEC, a human microvascular endothelial cell line, was purchased from Lonza and maintained in endothelial growth medium (EGM™-2MV BULLETKIT™; Clonetics) supplemented with 5% fetal bovine serum (FBS). Cells were maintained in a humidified environment containing 5% $CO_2$ at 37° C., and the culture medium was replaced every 2 days. Cells were permitted to attach for 24 h and to grow to 80% confluence and then cells were treated for 3 hours with serum free medium (CONTROL), FIXIONEAL™ 2.27% (containing as osmotic agent only glucose at 2.27% concentration) or XYLOCORE™ 1.5% (containing as osmotic agents glucose (0.5%), Xylitol (1.5%) and L-Carnitine (0.02%)).

Gene Expression Analysis

Total RNA was extracted from cell monolayers using the Trizol reagent (Invitrogen), according to the manufacturer's instructions. Yield and purity were checked using Nanodrop (EuroClone), and total RNA from each sample was reverse-transcribed into cDNA using SuperScript II™ Reverse Transcriptase (Invitrogen). Real-time PCR was performed on an ABI-Prism 7500™ using Power SYBR GREEN MASTER MIX 2×™ (Applied Biosystems). The comparative Ct method (DDCt) was used to quantify gene expression, and the relative quantification was calculated as 2-DDCt. The presence of non-specific amplification products was excluded by melting curve analysis. Real-time PCR data and statistics were calculated with the Rest2009™ software.

Results

As shown in the Table 5 below, experimental results showed that the commercial available peritoneal dialysis solution FIXIONEAL™ 2.27% significantly increase the expression of MMT/EndoMT transcription factors (SNAIL) and markers ($\alpha$-SMA) both in endothelial (HMVEC) and mesothelial (HMRSV5) cells. In the same way, FIXIONEAL™ 2.27% significantly increase the expression of apoptosis (BAX) and angiogenesis (VEGF) markers.

Gene expression analysis of endothelial and mesothelial treated with XYLOCORE™ solutions revealed a significant down-regulation of transcripts encoding for MMT/EndoMT biomarkers (SNAIL and $\alpha$-SMA) apoptosis and angiogenesis compared to FIXIONEAL™ solution with comparable osmotic strength.

heat-inactivated fetal bovine serum (FBS) and 100 U/mL penicillin/streptomycin (Invitrogen) and growth in type I collagen coated plastics. Cells were maintained in a humidified environment containing 5% CO2 at 37° C., and the culture medium was replaced every 2 days.

Cells were plated ($2*10^5$ cells/cm$^2$) in transwells and when a stable transepithelial resistances had been obtained the medium was removed, cells were washed with PBS and then treated for 8 hours with pure PoliCore, Extraneal or control solution and then refilled with medium for 24 hours.

Cells were plated on transwells in complete medium, washed once with PBS and then treated for 8 hours with serum free medium (CTR), PoliCore and Extraneal. Cell viability was ascertained after the various treatments using the CellTiter 96 Aqueous One Solution Cell Proliferation As-say [3-(4.5-dimethylthiazol-2-yl)-5-(3-carboxymethoxyphenyl)-2-(4-sulfophenyl)-2H-tetrazolium, inner salt; MTS] (Promega), according to the manufacturer's protocol. Briefly 20 µl of reagent was added to each well, the plate was incubated for 3 h at 37° C., then the absorbance was measured at 490 nm. Results were normalized to CTR which was set equal to 1.

TABLE 5

Results in HMVEC and HMRSV5 cells.

HMVEC |Human Microvascular Endothelial Cells|

| MARKER OF | | CONTROL | | FIXIONEAL 2.27% | | p FDC vs CONTROL | XYLOCORE 1.5% | | p XYLO vs CONTROL | p XYLO vs FIX |
|---|---|---|---|---|---|---|---|---|---|---|
| | | MEAN | S.D. | MEAN | S.D. | Rest-2009 © | MEAN | S.D. | Rest-2009 © | Rest-2009 © |
| EMT | SNAIL | 1.00 | 0.05 | 4.61 | 0.29 | p < 0.001 | 2.67 | 0.43 | p < 0.05 | p < 0.05 |
| EMT | a-SMA | 1.03 | 0.35 | 2.45 | 0.67 | p < 0.001 | 0.57 | 0.18 | | p < 0.05 |
| Apoptosis | BAX | 1.00 | 0.04 | 19.06 | 4.20 | p < 0.001 | 7.02 | 1.49 | p < 0.05 | p < 0.05 |
| Angiogenesis | VEGF | 1.00 | 0.14 | 21.30 | 4.95 | p < 0.001 | 4.03 | 0.66 | p < 0.05 | p < 0.001 |

HMRSV5 Human mesothelial cells

| MARKER OF | | CONTROL | | FIXIONEAL 2.27% | | p FDC vs CONTROL | XYLOCORE 1.5% | | p XYLO vs CONTROL | p XYLO vs FIX |
|---|---|---|---|---|---|---|---|---|---|---|
| | | MEAN | S.D. | MEAN | S.D. | Rest-2009 © | MEAN | S.D. | Rest-2009 © | Rest-2009 © |
| EMT | SNAIL | 1.00 | 0.12 | 32.67 | 7.96 | p < 0.001 | 2.01 | 0.14 | p < 0.05 | p < 0.001 |
| EMT | a-SMA | 1.00 | 0.09 | 2.75 | 0.44 | p < 0.05 | 1.49 | 0.23 | | p < 0.05 |
| Apoptosis | BAX | 1.00 | 0.13 | 1.89 | 0.56 | p < 0.05 | 1.38 | 0.19 | | |
| Angiogenesis | VEGF | 1.02 | 0.25 | 2.65 | 0.05 | P < 0.001 | 2.04 | 0.02 | p < 0.05 | p < 0.05 |

CONCLUSIONS

These experimental findings prove that a solution according to the present invention (XYLOCORE™) has a better effect than glucose based solutions with comparable osmotic strength in terms of MMT/EndoMT event that sustain fibrosis but also apoptosis and angiogenesis, events which favors the lose of peritoneal filtration capacity.

A number of embodiments of the invention have been described. Nevertheless, it can be understood that various modifications may be made without departing from the spirit and scope of the invention. Accordingly, other embodiments are within the scope of the following claims Example 3

Cell culture and treatments: human peritoneal mesothelial cells (HMrSV5), kindly obtained by Prof. Ronco P (Paris), were cultured in DMEM/F12 supplemented with 10% (v/v)

Cells were cultured in transwells and transepithelial resistance (TER) was measured daily using a Millicell-ERS ohmmeter with electrodes (Millipore) inserted on both sides of the filter. The alternating current applied between the electrodes was within 620 IA at a frequency of 12.5 Hz. The resistance of the monolayer was multiplied by the effective surface area to obtain the electrical resistance of the monolayer (X cm2). The background TER of the blank Transwell filter was subtracted from the TER of the cell monolayer. Once stable resistances had been obtained, different solutions were tested for 8 h and then cells were recovered in with medium. TER was measure 21 h after.

Total RNA was extracted using the Trizol reagent (Invitrogen), according to the manufacturer's instructions. Yield and purity were checked using Nanodrop (EuroClone), and total RNA from each sample was reverse-transcribed into cDNA using SuperScript II Reverse Transcriptase (Invitrogen). Real-time PCR was performed on an ABI-Prism 7500 using Power SYBR Green Master Mix 2× (Applied Biosystems). The comparative Ct method (DDCt) was used to quantify gene expression, and the relative quantification was calculated as $2^{-DDCt}$. The presence of non-specific amplification products was excluded by melting curve analysis. Real-time PCR data and statistics were calculated with the Rest2009 software.

Cells cultured in transwell and treated as described above were fixed in 4% paraformaldehyde and permeabilized, then incubated overnight at 4° C. with the primary antibodies (α-SMA from Sigma Aldrich) in PBS with 1% bovine serum albumin (BSA), and then washed three times for 5 min with PBS before incubation for 1 h at room temperature with the secondary antibody (Alexa fluor 546 Invitrogen), again in PBS with 1% BSA. Cell nuclei were visualized with a Hoechst 33258. Images were obtained with a confocal LeicaSP5 microscope.

For comparison between two distributions, the two-tailed t-test was used. For multiple comparisons, one-way analysis of variance (ANOVA) was used.

Experimental results showed that treatment with solution named PoliCore [1.5% w/v xylitol, 4.0 w/v polydextrin and 0.02% w/v carnitine] preserved cells viability and mesothelial layer integrity. On the other side, the commercially available peritoneal dialysis solution Extraneal significantly reduced mesothelial cells viability and seems to reduce also the integrity of mesothelial layer measured by TER (table 6).

TABLE 6

| | VIABILITY | | | TER % of CTR | | |
|---|---|---|---|---|---|---|
| | MEAN | S.D. | $*p < 0.05$; $**p < 0.01$ | MEAN | S.D. | $*p < 0.05$; $**p < 0.001$ |
| CONTROL | 1.00 | 0.14 | | 100.00 | 3.23 | |
| POLICORE | 1.06 | 0.04 | | 102.97 | 2.14 | |
| EXTRANEAL | 0.80 | 0.03 | ** | 94.55 | 4.32 | |

Results showed that mesothelial cells exposed to Extraneal exhibited a significant gene expression up-regulation of mesenchymal markers alpha-smooth muscle actin (α-SMA) and vimentin (VIM), as well as a reduction of E-cadherin (E-CAD), a key epithelial marker. The treatment with PoliCore did not induce any effect (tables 7-9).

TABLE 7

Relative α-SMA expression

| | MEAN | S.D. | $*p < 0.05$; $**p < 0.01$ |
|---|---|---|---|
| CONTROL | 1.00 | 0.03 | |
| POLICORE | 1.26 | 0.61 | |
| EXTRANEAL | 2.05 | 0.06 | ** |

TABLE 8

Relative VIM expression

| | MEAN | S.D. | $*p < 0.05$; $**p < 0.01$ |
|---|---|---|---|
| CONTROL | 1.00 | 0.13 | |
| POLICORE | 1.29 | 0.36 | |
| EXTRANEAL | 2.13 | 0.04 | * |

TABLE 9

Relative E-CAD expression

| | MEAN | S.D. | $*p < 0.05$; $**p < 0.01$ |
|---|---|---|---|
| CONTROL | 1.01 | 0.24 | |
| POLICORE | 1.28 | 0.12 | |
| EXTRANEAL | 0.35 | 0.08 | * |

The up-regulation of α-SMA protein by Extraneal treatment was confirmed also by immunofluorescence staining (data not shown). No α-SMA signal was detected after PoliCore treatment.

Since TGF-β is a master regulator of mesothelial to mesenchymal transition we analyzed its expression. Results showed that the treatment with both the solutions tested did nod modified TGF-β gene expression. These data could indicate that the up-regulation of α-SMA and VIM and the down-regulation of E-CAD by Extraneal may be regulated by mechanisms/signaling pathway other that TGF-β (table 10).

TABLE 10

Relative TGF-β expression

| | MEAN | S.D. | $*p < 0.05$; $**p < 0.01$ |
|---|---|---|---|
| CONTROL | 1.00 | 0.14 | |
| POLICORE | 1.13 | 0.07 | |
| EXTRANEAL | 0.93 | 0.02 | |

Another factor which contributes to ultrafiltration failure is vascular endothelial growth factor (VEGF), a potent pro-angiogenic factor. However, gene expression analysis did not reveal significant differences in mesothelial cells treated with PoliCore or Extraneal (table 11).

TABLE 10

Relative VEGF expression

| | MEAN | S.D. | $*p < 0.05$; $**p < 0.01$ |
|---|---|---|---|
| CONTROL | 1.01 | 0.23 | |
| POLICORE | 1.25 | 0.13 | |
| EXTRANEAL | 1.37 | 0.10 | |

What is claimed is:
1. A peritoneal dialysis solution comprising:
 (a) a lactate buffered solution comprising xylitol at about 1.5%, L-carnitine at about 0.02% and polydextrin at about 4.0%, or

(b) a lactate buffered solution comprising glucose at about 1.5%, L-carnitine at about 0.02% and xylitol at about 2.0%.

2. The peritoneal dialysis solution of claim 1, wherein the peritoneal dialysis solution comprises a lactate buffered solution consisting of xylitol at about 1.5%, L-carnitine at about 0.02% and polydextrin at about 4.0%.

3. The peritoneal dialysis solution of claim 1, wherein the peritoneal dialysis solution comprises a lactate buffered solution consisting of glucose at about 1.5%, L-carnitine at about 0.02% and xylitol at about 2.0%.

4. The peritoneal dialysis solution of claim 1, wherein the peritoneal dialysis solution has a pH comprised between about 5.5 and 7.5.

5. The peritoneal dialysis solution of claim 1, formulated as a continuous ambulatory peritoneal dialysis (CAPD) solution or an automatic peritoneal dialysis (APD).

6. The peritoneal dialysis solution of claim 1, formulated as a nocturnal exchange of peritoneal dialysis solution and/or one or more diurnal exchanges of peritoneal dialysis solution.

7. The peritoneal dialysis solution of claim 1, formulated as a concentrate or in dry form.

8. The peritoneal dialysis solution of claim 1, formulated as a concentrate or in dry form for administering in a peritoneal dialysis home machine.

9. The peritoneal dialysis solution of claim 1, formulated for administration once a day.

10. The peritoneal dialysis solution of claim 9, formulated for administration, twice, three times or four times or more a day.

11. The peritoneal dialysis solution of claim 1, formulated for administration intraperitoneally.

12. The peritoneal dialysis solution of claim 11, formulated for administration intraperitoneally, wherein each dose or dwell is at between about 1 to 3 liters, or between about 2 to 5 liters.

13. The peritoneal dialysis solution of claim 12, formulated for administration intraperitoneally, wherein each dose or dwell is between about 1 to 3 liters for CAPD, and between about 2 to 5 liters for APD.

* * * * *